(12) United States Patent
Liu

(10) Patent No.: US 11,534,009 B2
(45) Date of Patent: Dec. 27, 2022

(54) ELECTRONIC PAINTING FRAME AND SCENT RELEASE METHOD FOR ELECTRONIC PAINTING FRAME

(71) Applicant: BOE TECHNOLOGY GROUP CO., LTD., Beijing (CN)

(72) Inventor: Zijun Liu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 426 days.

(21) Appl. No.: 16/618,319

(22) PCT Filed: Mar. 25, 2019

(86) PCT No.: PCT/CN2019/079520
§ 371 (c)(1),
(2) Date: Nov. 29, 2019

(87) PCT Pub. No.: WO2019/184873
PCT Pub. Date: Oct. 3, 2019

(65) Prior Publication Data
US 2020/0093291 A1    Mar. 26, 2020

(30) Foreign Application Priority Data
Mar. 28, 2018 (CN) .......................... 201810264389.9

(51) Int. Cl.
*A47G 1/06* (2006.01)
*A61L 9/12* (2006.01)
*G06F 3/147* (2006.01)

(52) U.S. Cl.
CPC ............ *A47G 1/0616* (2013.01); *A61L 9/125* (2013.01); *G06F 3/147* (2013.01); *G09G 2354/00* (2013.01); *G09G 2380/16* (2013.01)

(58) Field of Classification Search
None
See application file for complete search history.

(56) References Cited

U.S. PATENT DOCUMENTS

| | | | |
|---|---|---|---|
| 7,946,064 B2 | 5/2011 | Liou et al. | |
| 9,723,905 B2 | 8/2017 | Kim et al. | |
| 2007/0299298 A1 | 12/2007 | Suissa et al. | |
| 2015/0130087 A1* | 5/2015 | Berard | A61L 9/122 261/26 |

(Continued)

FOREIGN PATENT DOCUMENTS

| | | |
|---|---|---|
| CN | 101084535 A | 12/2007 |
| CN | 101485529 A | 7/2009 |

(Continued)

*Primary Examiner* — Andre L Matthews

(57) ABSTRACT

An electronic picture frame and an odor releasing method thereof are provided. The electronic picture frame includes: a picture frame body having a display screen on the picture frame body; an odor releasing device disposed on the picture frame body and configured to release a plurality of different odors; and a processing device connected with the display screen and the odor releasing device, respectively, and configured to acquire material type information of a picture displayed on the display screen (2), and control the odor releasing device to release an odor corresponding to the material type information according to the material type information of the picture.

13 Claims, 4 Drawing Sheets

(56) References Cited

U.S. PATENT DOCUMENTS

2015/0351518 A1* 12/2015 Kim .................... B05B 12/124
              222/1
2020/0093291 A1   3/2020 Liu

FOREIGN PATENT DOCUMENTS

| CN | 103475938 A | 12/2013 |
| CN | 204149760 U | 2/2015 |
| CN | 204467609 U | 7/2015 |
| CN | 105164614 A | 12/2015 |
| CN | 108470517 A | 8/2018 |
| JP | 2000267611 A | 9/2000 |
| TW | 200900785 A | 1/2009 |

* cited by examiner

ELECTRONIC PAINTING FRAME AND SCENT RELEASE METHOD FOR ELECTRONIC PAINTING FRAME

TECHNICAL FIELD

Embodiments of the present disclosure relate to an electronic picture frame and an odor releasing method thereof.

BACKGROUND

With the continuous development of the electronic industry, the use of electronic products is increasingly widespread. As a new form of information display, electronic display devices can cyclically display digitally stored information in various modes, and thus have been applied in more and more fields.

Traditional pictures are usually stored and displayed in the form of paper, however, with the popularity of electronic display methods, more and more pictures are digitally stored and displayed through electronic display method, which overcomes the shortcomings of traditional paper pictures that display content is single and damage occurs easily.

SUMMARY

At least one embodiment of the present disclosure provides an electronic picture frame and an odor releasing method of the electronic picture frame, which can release an odor of a picture material while displaying the picture, thereby providing a better viewing experience for the viewer.

To achieve the above objective, the embodiments of the present disclosure mainly adopt the following technical solutions.

On one aspect, embodiments of the present disclosure provide an electronic picture frame, which includes: a picture frame body provided with a display screen; an odor releasing device disposed on the picture frame body and configured to release a plurality of different odors; and a processing device connected with the display screen and the odor releasing device, respectively, and configured to acquire material type information of a picture displayed on the display screen and to control the odor releasing device to release an odor corresponding to the material type information according to the material type information of the picture.

In an optional embodiment, the electronic picture frame further includes: a distance detection device, the distance detection device is connected with the processing device and configured to detect an active distance between a viewer and the picture frame body; the processing device is configured to control the odor releasing device to release the odor corresponding to the material type information according to the material type information of the picture in the case where the active distance is less than or equal to a predetermined distance; and the processing device is configured to control the odor releasing device to stop releasing the odor in the case where the active distance is greater than the predetermined distance.

In an optional embodiment, the processing device is further configured to control an amount of odor released by the odor releasing device according to the active distance in the case where the active distance is less than or equal to the predetermined distance.

In an optional embodiment, the odor releasing device includes an execution device including a fan and an odor source, the odor source is disposed at an air outlet of the fan, the fan includes a control terminal, the control terminal is connected with the processing device, and the processing device is further configured to control a rotating speed of the fan.

In an optional embodiment, the odor releasing device includes a plurality of execution devices, and types of odors of the odor sources in the plurality of execution devices are different from each other.

In an optional embodiment, the odor releasing device further includes a heating member disposed on the odor source and connected with the processing device, and the processing device is further configured to control a heating temperature of the heating member.

In an optional embodiment, the odor source is any one selected from the group consisting of an oil ink odor source, an ink odor source, a watercolor odor source, a gouache odor source, a propylene odor source, and a pencil odor source.

In an optional embodiment, the picture frame body is provided with a plurality of receiving grooves, each of the plurality of receiving grooves is provided with one of the execution devices, the air outlet of the fan in the execution device faces an opening of the receiving groove to which the execution device belongs, and a shielding net is disposed on the opening of the receiving groove to shield the execution device in the receiving groove.

In an optional embodiment, the electronic picture frame further includes: a storage device, the storage device is connected with the display screen and is configured to store picture information and the material type information corresponding to the picture information, and the display screen is configured to display the picture information and transmit the material type information corresponding to the picture information to the processing device.

In an optional embodiment, the electronic picture frame further includes a network device connected with the display screen, the display screen is further configured to acquire, by the network device, picture information and the material type information corresponding to the picture information so as to display the picture information and transmit the material type information corresponding to the picture information to the processing device.

In an optional embodiment, each of the odor sources is any one selected from the group consisting of a liquid odor source, a solid odor source and a gel odor source.

On the other aspect, embodiments of the present disclosure provide an odor releasing method of the electronic picture frame described above, which includes: acquiring the material type information of the picture to be displayed; and releasing an odor corresponding to the material type information according to the material type information.

In an optional embodiment, releasing the odor corresponding to the material type information according to the material type information includes: acquiring an active distance between a viewer and the electronic picture frame; releasing an odor corresponding to the material type information according to the material type information in the case where the active distance is less than or equal to a predetermined distance; and stopping releasing the odor in the case where the active distance is greater than the predetermined distance.

BRIEF DESCRIPTION OF THE DRAWINGS

The above and/or other aspects and advantages of the present disclosure will become apparent and easy to understand with reference to the embodiments in connection with the drawings below. In the accompanying drawings.

DETAILED DESCRIPTION

In order to make objectives, technical solutions and advantages of the embodiments of the disclosure apparent, the technical solutions of the embodiments will be described in a clearly and fully understandable way in connection with the drawings related to the embodiments of the present disclosure. Apparently, the described embodiments are just a part but not all of the embodiments of the present disclosure. Based on the described embodiments herein, those skilled in the art can obtain other embodiment(s), without any inventive work, which should be within the scope of the present disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for invention, are not intended to indicate any sequence, amount or importance, but distinguish various components. Also, the terms such as "a," "an," etc., are not intended to limit the amount, but indicate the existence of at least one. The terms "comprise," "comprising," "include," "including," etc., are intended to specify that the elements or the objects stated before these terms encompass the elements or the objects and equivalents thereof listed after these terms, but do not preclude the other elements or objects. "On," "under," and the like are only used to indicate relative position relationship, and when the position of the described object is changed, the relative position relationship may be changed accordingly.

An electronic picture frame and an odor releasing method of the electronic picture frame provided by the embodiments of the present disclosure are further described in detail below with reference to the accompanying drawings and embodiments.

The inventor(s) of the present application found in the research that displaying a picture in an electronic display manner can only display the content of the picture. However, as a carrier of artistic information, a material type and an odor of the picture itself are also very important for the viewing experience of the viewer, in addition to the content of the picture.

Figure 1:
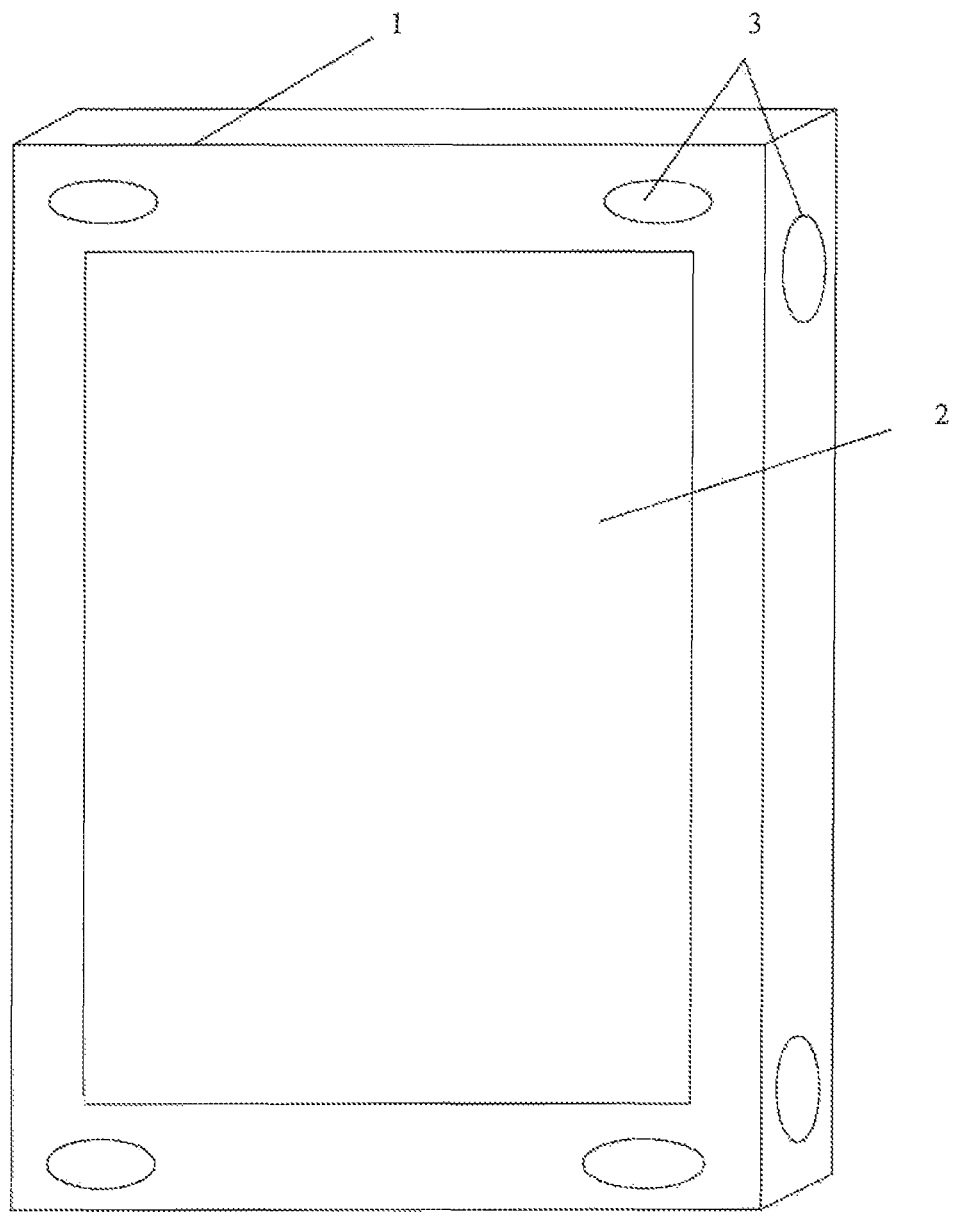
FIG. 1 is a schematic view illustrating a structure of an electronic picture frame provided by an embodiment of the present disclosure.

On one aspect, as illustrated in FIG. 1, an embodiment of the present disclosure provides an electronic picture frame, which includes: a picture frame body 1 having a display screen 2 on the picture frame body 1; an odor releasing device 3 disposed on the picture frame body 1 and configured to release a plurality of different odors; and a processing device (not illustrated) connected with the display screen 2 and the odor releasing device 3, respectively, and configured to: acquire material type information of a picture displayed on the display screen 2, and control the odor releasing device 3 to release an odor corresponding to the material type information according to the material type information of the picture.

In the electronic picture frame provided by the embodiment of the present disclosure, the display screen 2 is configured to electronically display the picture, and the display screen 2 may be directly disposed on a surface of one side of the picture frame body 1 or may be embedded in a groove provided on the picture frame body. The display screen 2 can, for example, cyclically display (play) different pictures, and an adjustment button may be provided on the picture frame body 1 for the viewer to adjust a display sequence of the pictures and a display time of each of the pictures by the adjustment button. The picture frame body 1 may be in various shapes and made of various materials. For example, the picture frame body 1 may be in a form of a picture scroll, and the display screen 2 is disposed in a framed region of the picture scroll; or the picture frame body 1 may be in a form of a photo frame, and the display screen 2 is embedded in an exhibit region of the photo frame. Before electronically displaying a picture, the picture is digitized firstly, and then content information of the picture and material type information corresponding to the picture are obtained to determine the type of odor to be released by the odor releasing device 3 according to the material type information. The processing device is connected with the display screen 2 and the odor releasing device 3, respectively; as a result, when the display screen 2 electronically displays one of the pictures according to the content information of the picture, the processing device can acquire the material type information corresponding to the picture and control the odor releasing device 3 to releases an odor corresponding to the material type information, so that the viewer can smell the odor corresponding to the material used for the picture while viewing the picture. The odor releasing device 3 may be disposed at any position of the picture frame body 1, and one or more odor releasing device 3 may be provided. For example, the picture frame body 1 may be in a flat plate structure, and the odor releasing device 3 is disposed on a surface of a side of the picture frame body facing the display screen or is disposed on a surface of a side of the picture frame body facing away from the display screen; or, the picture frame body 1 may be in a form of a picture scroll, and the odor releasing device 3 is placed on at least one of picture axes at both ends of the picture scroll.

As compared with the known technology in which only the display content of the picture is provided, the electronic picture frame provided by the embodiment of the present disclosure can acquire the material type information of the picture and release the odor corresponding to the material type information while displaying the picture electronically. Therefore, when the viewer views the picture, not only the content of the picture can be seen through the display screen, but also the odor of the material used in the picture is smelled, thereby creating a more realistic viewing environment for the viewer, improving the viewing experience of the viewer, and increasing the use value of the electronic picture frame.

In an optional embodiment, the electronic picture frame further includes a distance detection device, and the distance detection device is connected with the processing device and configured to detect an active distance of a viewer or a passerby from the picture frame body 1. In the case where the active distance is less than or equal to a predetermined distance, the processing device controls the odor releasing device to release an odor corresponding to the material type information according to the material type information of the picture. In the case where the active distance is greater than the predetermined distance, the processing device controls the odor releasing device to stop releasing the odor.

In an optional embodiment, the processing device may also control an amount of odor released by the odor releasing device according to the active distance in the case where the active distance is less than or equal to the predetermined distance.

For example, a first distance threshold and a second distance threshold may be provided, and the first distance threshold is greater than the second distance threshold. In the case where a distance between a viewer or a passerby of the electronic picture frame and the picture frame body 1 is greater than the first distance threshold, the odor may not be released because the viewer is far away from the picture. In the case where a distance between a viewer or a passerby and the picture frame body 1 is less than the first distance and is greater than the second distance threshold, the viewer is closer to the picture frame, and a large dose of odor may be released, so that the viewer who is viewing the picture can smell the picture. In the case where a distance between a viewer and the picture frame body 1 is less than the second distance threshold, it means that the viewer may be observing the picture at an extremely close distance; at this time, a small dose of odor can be released so that the viewer can smell the odor evenly when viewing the picture at different positions. Furthermore, adjusting the odor release amount according to the distance between the viewer and the picture can also save odor consumables. The distance detection device in the embodiment of the present disclosure may be implemented by various devices known in the art that can implement the above functions, such as an infrared sensor or the like, without repeated herein.

Figure 2:
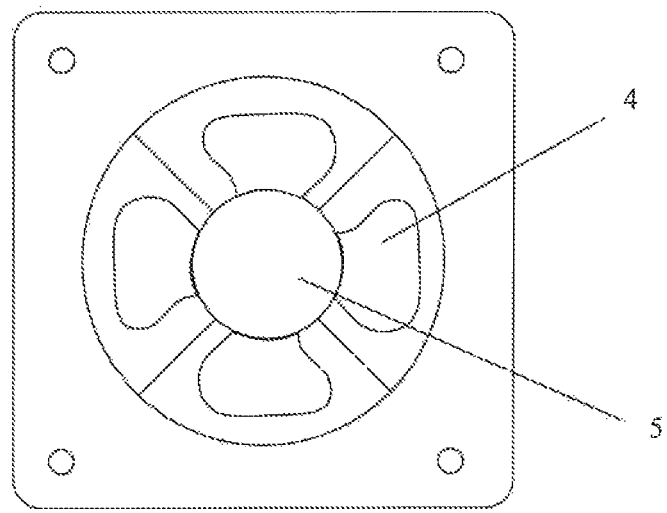
FIG. 2 is a schematic view illustrating a structure of an execution device of an electronic picture frame provided by an example of an embodiment of the present disclosure.

In an optional embodiment, as illustrated in FIG. 2, the above-described odor releasing device may include an execution device including a fan 4 and an odor source 5, and the odor source 5 is disposed at an air outlet of the fan 4, and a control terminal of the fan 4 is connected with the processing device. When it needs to release an odor, the processing device controls, through the control terminal, the fan 4 to rotate so as to generate a certain amount of air to be blown to the odor source 5, thereby releasing the odor. In some examples, the processing device can also control a speed at which the fan 4 rotates according to the distance between the viewer and the electronic picture frame. For example, in the case where the distance between the viewer and the picture frame body 1 is greater than the first distance threshold, the processing device controls, through the control terminal, the fan 4 to stop rotating; in the case where the distance between the viewer and the picture frame body 1 is less than the first distance threshold and greater than the second distance threshold, the processing device controls, through the control terminal, the fan 4 to rotate at a larger speed; and in the case where the distance between the viewer and the picture frame body 1 is less than the second distance threshold, the processing device controls, through the control terminal, the fan 4 to rotate at a smaller speed. As a result, a rotation speed of the fan can be adjusted according to the distance between the viewer and the picture, thereby meeting the requirements for different odor release amounts in different situations.

In some examples, the above-described odor releasing device may include a plurality of execution devices, and the types of odors of the odor sources in the plurality of execution devices are different from each other. Thus, when the display screen displays a picture, the processing device can control the execution device including a corresponding odor source to release odor according to the material type information of the picture.

Figure 3:
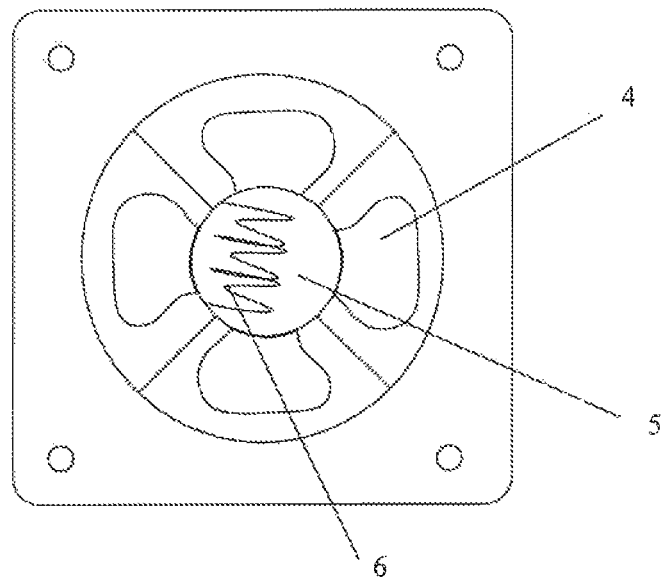
FIG. 3 is a schematic view illustrating a structure of an execution device of an electronic picture frame provided by another example of an embodiment of the present disclosure.

In an optional embodiment, as illustrated in FIG. 3, the odor releasing device may further include a heating member 6 disposed on the odor source 5 and connected with the processing device. When it needs to release an odor, the processing device controls the heating member 6 to operate to generate heat to heat the odor source 5, thereby releasing the odor. In some examples, the processing device can control a heating power of the heating member 6 according to the distance between the viewer and the picture frame, thereby controlling the odor release amount. The heating member 6 may be provided separately in the execution device or may be provided in the execution device in combination with the fan 4 described above. For example, in the case where a size of the picture to be displayed is large and the number of execution devices is small, a large amount of odor cannot be generated merely by relying on the fan, and the heating member 6 can be used as an aid. In the case where a large amount of odor is required, the heating member 6 is controlled to heat the odor source 5 at a higher power while a large amount of air is blown to the odor source by the fan, thereby realizing rapid, mass production of odor. In addition, the combined use of the fan 4 and the heating member 6 also increases the accuracy on adjustment of odor release amount.

In embodiments of the present disclosure, the execution device can produce a variety of odors by placing different odor sources. For example, the odor source may be any one of an oil ink odor source, an ink odor source, a watercolor odor source, a gouache odor source, a propylene odor source and a pencil odor source. For example, when the display screen displays an ink painting, the processing device controls the execution device provided with the ink odor source to release odor, enabling the viewer to smell the ink while viewing the ink painting.

In an embodiment of the present disclosure, the odor source may be any one of a liquid odor source, a solid odor source, and a gel odor source. Different materials have different volatilization rates, so different concentrations of odor can be provided. For example, in the case where the picture is a pencil drawing, because an odor of the pencil drawing is lighter than that of an ink painting, a gel odor source scented with a pencil odor can be used to release a lighter pencil odor, so as to simulate an environment in which a real pencil drawing is actually viewed. For another example, in situations where a higher concentration of odor is desired, a liquid odor source can be used and the liquid odor source can be heated so that the odor source can rapidly produce a large amount of odor.

Figure 4:
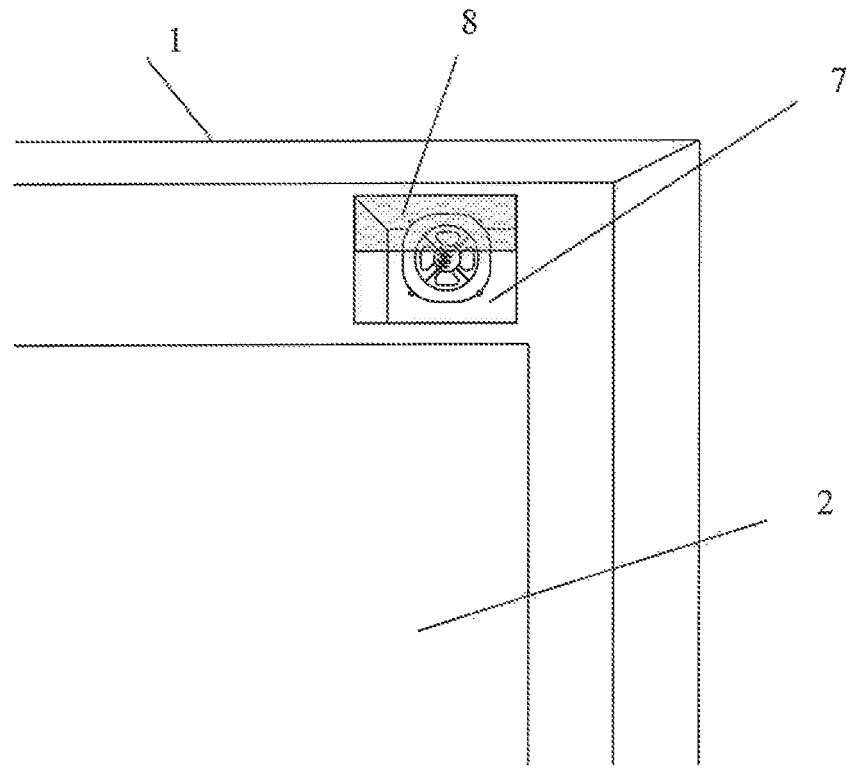
FIG. 4 is a schematic view illustrating a partial structure of an electronic picture frame provided by an embodiment of the present disclosure.

In an optional embodiment, as illustrated in FIG. 4, the picture frame body 1 may be provided with a plurality of receiving grooves 7, each of the receiving grooves 7 may be provided with one execution device, and an air outlet of a fan 4 in the execution device faces an opening of the receiving groove 7 in which the fan 4 is located. As a result, the odor generated by the execution device can be released outward through the opening of the receiving groove 7. An appearance of the electronic picture frame can be made more clean and tidy by arranging the execution device in the receiving groove 7. At the same time, the odor generated by the execution device can be released only through the opening of the receiving groove 7, thereby avoiding the shortcomings such as decentralized release of order and unstable release direction of odor in the case where the execution device is separately placed.

For example, the opening of the receiving groove 7 may be provided with a shielding net 8 to shield the execution device in the receiving groove 7. The shielding net 8 can be freely moved at the opening of the receiving groove 7, and one end of the shielding net 8 is provided with a control device connected with the processing device, and an area of the receiving groove 7 shielded by the shielding net 8 can be controlled according to different requirements of odor release amount, so as to achieve adjustment on the odor release amount. For example, in the case where neither a fan 4 nor a heating member 6 is provided in the execution device, and the odor is generated only by the volatilization of the odor source 5, the odor release amount can be adjusted by adjusting a covering area of the shielding net 8 covering the opening of the receiving groove 7. Therefore, the diversity in adjustment of the odor release amount is provided.

In an optional embodiment, the electronic picture frame may further include a storage device connected with the display screen 2 and configured to store the picture information and material type information corresponding to the picture information. When it is necessary to electronically display the picture, the display screen 2 acquires the picture information and the material type information corresponding to the picture information from the storage device, thereby displaying the picture according to the picture information, and simultaneously transmitting the material type information corresponding to the picture being displayed; and the processing device further selects the corresponding execution device to release odor according to the material type information.

In an optional embodiment, the picture information and the material type information corresponding to the picture information may be acquired by a local storage device or may be acquired by a network device. The network device may be connected with a cloud terminal or a remote control terminal. The network device is connected with the display screen 2, so that the display screen 2 can acquire the picture information and the material type information corresponding to the picture information that are stored in the cloud terminal or the remote control terminal through the network. The display screen 2 displays the picture according to the picture information, and transmits the material type information corresponding to the picture to a processing device, and the processing device further controls a corresponding execution device to release odor according to the material type information. In the embodiment of the present disclosure, the picture information and the material type information corresponding to the picture information are acquired by the network device, so as to realize information sharing, increase the diversity of the display screen 2 for displaying pictures, and meanwhile eliminating the need of arranging a storage device on the electronic picture frame to avoid occupying a space in the picture frame body 1.

In an optional embodiment, when the material type information does not have a corresponding execution device, the processing device can randomly activate an execution device for odor release.

Figure 5:
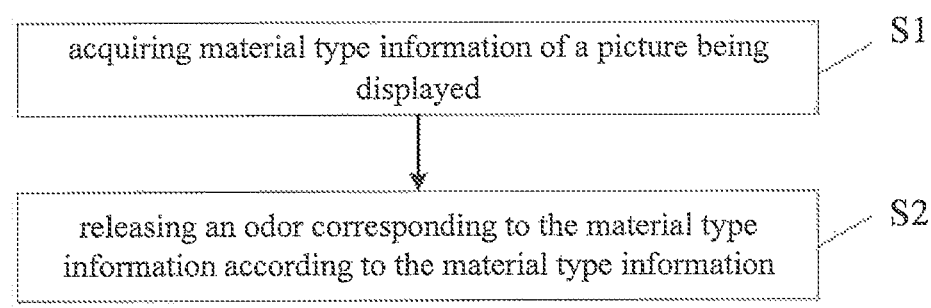
FIG. 5 is a schematic flowchart of an odor releasing method of an electronic picture frame provided by an embodiment of the present disclosure.

On the other aspect, as illustrated in FIG. 5, an embodiment of the present disclosure further provides an odor releasing method of an electronic picture frame, which is used in the electronic picture frame described in any of the above embodiments or examples, and the method may include:

S1: acquiring material type information of a picture being displayed; and

S2: releasing an odor corresponding to the material type information according to the material type information.

As compared with the known technology in which only the display content of the picture is provided, the odor releasing method of the electronic picture frame provided by the embodiment of the present disclosure can acquire the material type information of the picture and release an odor corresponding to the material type information while displaying the picture. As a result, when the viewer views the picture, not only the content of the picture can be seen through the display screen, but also the odor of the material used in the picture is smelled, thereby creating a more realistic viewing environment for the viewer, improving the viewing experience of the viewer and increasing the use value of the electronic picture frame.

Figure 6:
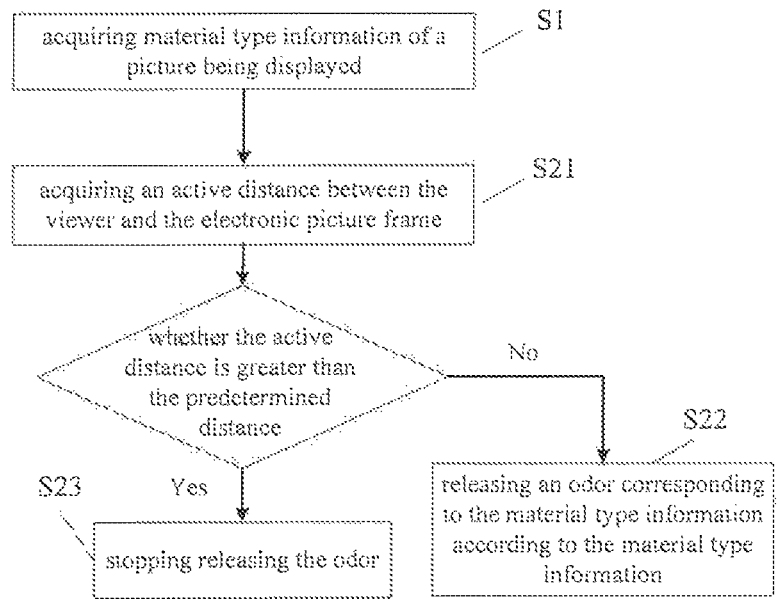
FIG. 6 is a schematic flowchart of an odor releasing method of an electronic picture frame provided by another embodiment of the present disclosure.

In an optional embodiment, as illustrated in FIG. 6, releasing the odor corresponding to the material type information according to the material type information may include:

S21: acquiring an active distance between the viewer and the electronic picture frame;

S22: releasing an odor corresponding to the material type information according to the material type information in the case where the active distance is less than or equal to a predetermined distance; and S23: stopping releasing the odor in the case where the active distance is greater than the predetermined distance.

Figure 7:
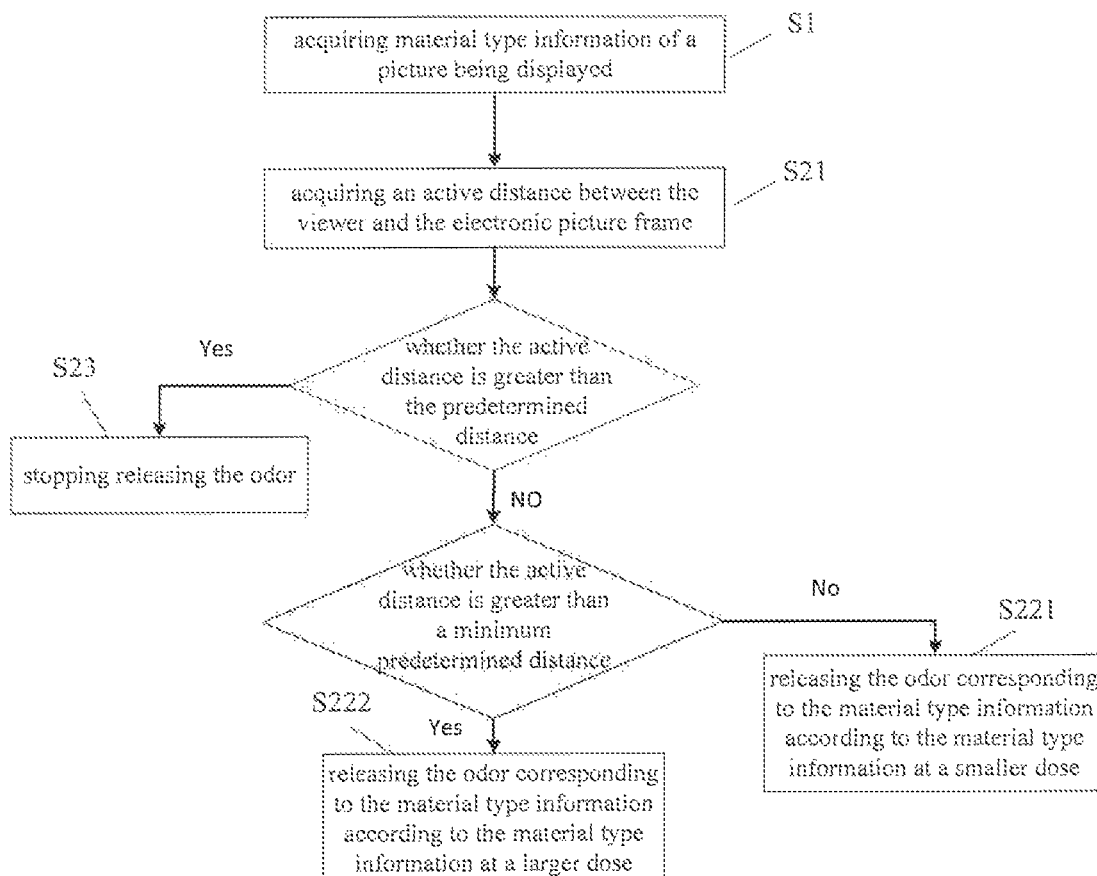
FIG. 7 is a schematic flowchart of an odor releasing method of an electronic picture frame provided by still another embodiment of the present disclosure.

In an optional embodiment, as illustrated in FIG. 7, releasing the odor corresponding to the material type information according to the material type information in the case where the active distance is less than or equal to the predetermined distance may include:

S221: releasing the odor corresponding to the material type information according to the material type information at an odor release amount higher than a predetermined threshold in the case where the active distance is less than or equal to the predetermined distance and greater than a minimum predetermined distance; and S222: releasing the odor corresponding to the material type information according to the material type information at an odor release amount less than or equal to the predetermined threshold in the case where the active distance is less than or equal to the minimum predetermined distance.

For example, in the case where the active distance is greater than the predetermined distance, it means that the viewer is far away from the picture, and no odor will be released at this time; in the case where the active distance is less than or equal to the predetermined distance, it means that the viewer is closer to the picture frame, and an amount of odor released by the odor releasing device can be further controlled according to the active distance. For example, in the case where the active distance is greater than a minimum predetermined distance, it means that the viewer may observe the entire picture at a suitable position closer to the picture frame, and at this time, the odor is released at a larger dose, so that the viewer viewing the picture smells the odor of the picture; in the case where the active distance is less than or equal to the minimum predetermined distance, it means that the viewer may observe the details of the picture at an extremely close distance, and at this time, the odor is released at a smaller dose, so that a concentration of odor smelled by the viewer viewing the picture at different positions is uniform. Furthermore, adjusting the odor release amount according to the distance between the viewer and the picture frame can also save odor consumables. In the embodiments of the present disclosure, the above-mentioned larger dose and smaller dose refer to a dose higher than a predetermined threshold and a dose lower than or equal to a predetermined threshold, respectively. For example, the predetermined threshold may refer to the dose of odor that can be sensed by the viewer according to the surrounding environment of the picture frame and the physiology of the human body.

Through the description of the above embodiments, those skilled in the art can clearly understand that the embodiments of the present disclosure can be implemented by means of a combination of software and necessary general hardware, and of course, can also be implemented only by hardware, but in many cases the former is a better implementation. Based on such understanding, portions of the technical solutions of the embodiments of the present disclosure that contribute in essence or to the known art may be embodied in the form of a software product stored in a readable storage medium, such as a floppy disk, a hard disk or an optical disk, etc. of a computer, and includes instructions for causing a computer device (which may be a personal computer, server, or network device, etc.) to perform the methods described in various embodiments of the present disclosure.

The above are merely exemplary embodiments of the present disclosure, and are not intended to limit the scope of the present disclosure. The scope of the present disclosure is defined by the appended claims.

The application claims priority to the Chinese patent application No. 201810264389.9, filed on Mar. 28, 2018, the entire disclosure of which is incorporated herein by reference as part of the present application.

What is claimed is:

1. An electronic picture frame comprising:
   a picture frame body provided with a display screen;
   an odor releasing device disposed on the picture frame body and configured to release a plurality of different odors; and
   a processing device connected with the display screen and the odor releasing device, respectively, and configured to acquire material type information of a picture displayed on the display screen and to control the odor releasing device to release an odor corresponding to the material type information according to the material type information of the picture, wherein
   the odor releasing, device comprises a plurality of execution devices each comprising a fan and an odor source, the odor source is disposed at an air outlet of the fan;
   the picture frame body is provided with a plurality of receiving grooves, and each of the plurality of receiving grooves is provided with one of the plurality of execution devices, and the air outlet of the fan in the execution device faces an opening of the receiving groove to which the execution device belongs, and
   a shielding net is disposed on the opening of the receiving groove to shield the execution device in the receiving groove.

2. The electronic picture frame according to claim 1, further comprising: a distance detection device, wherein
   the distance detection device is connected with the processing device and configured to detect an active distance between a viewer and the picture frame body,
   the processing device is configured to control the odor releasing device to release the odor corresponding to the material type information according to the material type information of the picture in the case where the active distance is less than or equal to a predetermined distance, and
   the processing device is configured to control the odor releasing device to stop releasing the odor in the case where the active distance is greater than the predetermined distance.

3. The electronic picture frame according to claim 2, wherein the processing device is further configured to control an amount of odor released by the odor releasing device according to the active distance in the case where the active distance is less than or equal to the predetermined distance.

4. The electronic picture frame according to claim 3, wherein
   the fan comprises a control terminal, and the control terminal is connected with the processing device, and
   the processing device is further configured to control a rotating speed of the fan.

5. The electronic picture frame according to claim 4, wherein types of odors in the odor sources in the plurality of execution devices are different from each other.

6. The electronic picture frame according to claim 4, wherein the odor releasing device further comprises a heating member disposed on the odor source and connected with the processing device, and
   the processing device is further configured to control a heating temperature of the heating member.

7. The electronic picture frame according to claim 6, wherein the odor source is any one selected from the group consisting of an oil ink odor source, an ink odor source, a watercolor odor source, a gouache odor source, a propylene odor source, and a pencil odor source.

8. The electronic picture frame according to claim 1, further comprising: a storage device, wherein
   the storage device is connected with the display screen and is configured to store picture information and the material type information corresponding to the picture information, and wherein
   the display screen is configured to display the picture information, and transmit the material type information corresponding to the picture information to the processing device.

9. The electronic picture frame according to claim 1, further comprising: a network device connected with the display screen, wherein
   the display screen is configured to acquire, by the network device, picture information and the material type information corresponding to the picture information, so as to display the picture information and transmit the material type information corresponding to the picture information to the processing device.

10. The electronic picture frame according to claim 6, wherein each of the odor sources is any one selected from the group consisting of a liquid odor source, a solid odor source and a gel odor source.

11. An odor releasing method of the electronic picture frame according to claim 1, comprising:
    acquiring the material type information of the picture to be displayed; and releasing an odor corresponding to the material type information according to the material type information.

12. The odor releasing method of the electronic picture frame according to claim 11, wherein releasing the odor corresponding to the material type information according to the material type information comprises:
    acquiring an active distance between a viewer and the electronic picture frame;
    releasing an odor corresponding to the material type information according to the material type information in the case where the active distance is less than or equal to a predetermined distance; and
    stopping releasing the odor in the case where the active distance is greater than the predetermined distance.

13. The odor releasing method of the electronic picture frame according to claim 11, wherein releasing the odor corresponding to the material type information according to the material type information in the case where the active distance is less than or equal to the predetermined distance comprises:
    releasing the odor corresponding to the material type information according to the material type information at an odor release amount higher than a predetermined threshold in the case where the active distance is less than or equal to the predetermined distance and greater than a minimum predetermined distance; and
    releasing the odor corresponding to the material type information according to the material type information at an odor release amount less than or equal to the predetermined threshold in the case where the active distance is less than or equal to the minimum predetermined distance.

* * * * *